US009463217B1

(12) United States Patent
Colin Aronovicz et al.

(10) Patent No.: US 9,463,217 B1
(45) Date of Patent: Oct. 11, 2016

(54) METHODS AND PHARMACEUTICAL COMPOSITIONS FOR TREATMENT OF RETINAL OCCLUSION (71) Applicant: Institut National de la Sante et de la Recherche Medicale, Paris (FR)

(72) Inventors: Yves Colin Aronovicz, Paris (FR); Olivier Hermine, Paris (FR); Marie-Paule Wautier, Paris (FR); Jean-Luc Wautier, Paris (FR); Emmanuel Heron, Paris (FR)

(73) Assignees: Institut National de la Santé et de la Recherche Médicale (INSERM), Paris (FR); Université Paris Descartes—Paris V, Paris (FR); Université Paris Diderot—Paris VII, Paris (FR); Université des Antilles et de la Guyane, Pointe-à-Pitre (FR); Institut National de la Transfusion Sanguinge (INTS), Paris (FR); Assistance Publique—Hôpitaux de Paris, Paris (FR); CHN OPHTALMOLOGIE QUINZE-VINGTS, Paris (FR)

( * ) Notice: Subject to any disclaimer, the term of this patent is extended or adjusted under 35 U.S.C. 154(b) by 728 days.

(21) Appl. No.: 13/762,482

(22) Filed: Feb. 8, 2013

Related U.S. Application Data (60) Provisional application No. 61/597,231, filed on Feb. 10, 2012.

(51) Int. Cl.
A61K 38/16 (2006.01)
A61K 38/17 (2006.01)
A61K 39/395 (2006.01)

(52) U.S. Cl.
CPC ............ *A61K 38/17* (2013.01); *A61K 39/3955* (2013.01)

(58) Field of Classification Search
None
See application file for complete search history.

(56) References Cited

U.S. PATENT DOCUMENTS

2006/0228299 A1* 10/2006 Thorpe ............ A61K 47/48415
424/1.49
2007/0025957 A1* 2/2007 Rosenblum .......... A61K 9/0048
424/85.1

OTHER PUBLICATIONS

Rand et al.(J Thromb Haemost, 2012 10(6):1109-19).*

* cited by examiner

*Primary Examiner* — Sharon Wen
(74) *Attorney, Agent, or Firm* — Whitham, Curtis & Cook, P.C.

(57) ABSTRACT

The present invention relates to methods and compositions for the treatment of retinal vein occlusion.

2 Claims, 4 Drawing Sheets

METHODS AND PHARMACEUTICAL COMPOSITIONS FOR TREATMENT OF RETINAL OCCLUSION

CROSS-REFERENCE TO RELATED APPLICATIONS

This application claims priority to US Provisional Application 61/597,231 filed Feb. 10, 2012.

FIELD OF THE INVENTION

The present invention relates to methods and compositions for the treatment of retinal vein occlusion.

BACKGROUND OF THE INVENTION

Retinal vein occlusion (RVO) is a common cause of permanent visual loss and is the fifth cause of unilateral blindness in an Australian population-based study W. The most frequent and less severe type, branch retinal vein occlusion (BRVO) [2], is possibly driven by a mechanical factor because it generally occurs at an arteriovenous crossing [3]. The most rare and sight-threatening form, central retinal vein occlusion (CRVO) [2], remains of unknown pathophysiology [4,5].

Aging, arterial hypertension and glaucoma are the only well-established risk factors for RVO [6-8]. Despite a number of studies, thrombophilic risk factors have not been found to be associated with RVO, which suggests a very limited role of coagulation or anticoagulation factors in the pathophysiology of the disease [5,9]. In contrast, substantial data exist suggesting that blood hyperviscosity is an important risk factor. Several blood viscosity parameters have been shown to be increased in RVO patients compared with normal subjects, including a higher hematocrit, higher whole blood viscosity, reduced red cell deformability, and enhanced index of erythrocyte aggregation [7,10-14].

About 27% of patients with CRVO exhibit spontaneous in vitro growth of erythroid precursors in the absence of any detectable myeloproliferative disorder [15]. Red blood cells (RBCs) from patients with polycythemia vera have an abnormal CD239 (Lu/BCAM) phosphorylation, which is responsible for abnormal interactions with endothelial cells [16]. It was previously demonstrated that abnormal erythrocyte adhesion correlated with retinopathy in diabetes mellitus [17] and with vascular occlusion in sickle cell anemia [18].

There is no disclosure in the art of the increase of RBC adhesion to endothelial cells in CRVO, nor the role of PS or PS receptor in the increased CRVO RBC adhesion, nor the use of agent that inhibits the binding of phosphatidylserine to phosphatidylserine receptor in methods for treatment of retinal vein occlusion.

However, there is a need to develop new drugs that will be suitable for treatment of retinal vein occlusion. In this way, it has been suggested that characterisation of new therapeutic targets against RBC adhesion to endothelial cells in RVO may be highly desirable.

SUMMARY OF THE INVENTION

The present invention relates to methods and pharmaceutical compositions for preventing and treating a retinal vein occlusion in a subject of need thereof.

FIGURES

FIG. 1: (A) Red blood cells (RBCs) from patients with central retinal vein occlusion (CRVO) (n=20) adhere in greater numbers on human microvascular endothelial cells (HMEC) than do RBCs from patients with retinal artery occlusion=4) or RBCs from healthy volunteers (controls, n=25) (***P<0.001) under static conditions. The unbroken line within the box represents the median; the dotted line represents the mean. The vertical lines extending beyond the boxes indicate the 25% and 75% percentiles, while the horizontal bars outside the boxes represent the 10% and 90% percentiles. The open circles indicate the values outside this range. (B) RBCs from patients with CRVO (n=20) adhere more efficiently to HMEC than RBCs from healthy volunteers (n=25) under flow conditions and are resistant to washout by increasing shear stress (P<0.001). The more adherent were RBCs from patients with Type 2 diabetes (n=60); adhesion of RBCs from patients with polycythemia vera (PV, n=38) was higher at low shear stress but was similar to that of patients with CRVO at 0.2 and 0.3 Pa.

FIG. 3: (A) Adhesion to human microvascular endothelial cells of red blood cells (RBCs) from patients with central retinal vein occlusion (n=10) was measured under static conditions in the presence or absence of antibodies or peptides. Anti-phosphatidylserine (PS) receptor antibody blocked adhesion up to 50%, while anti-stabilin-2, anti-CD36 and peptide PS receptor (PSR) ligand blocked adhesion up to 35%. Annexin V (n=16) inhibited adhesion by 35%. Bars denote SEM. *P<0.001, P<0.01, *P<0.05 vs. medium. (B) In flow conditions the different antibodies inhibited adhesion. Anti-PSR and PSR peptide exhibited a high inhibitory effect at 0.1 Pa (62%±8% and 70%±4%, respectively); at 0.3 Pa anti-stabilin and PSR peptide were in the same range of inhibition (43%±3 and 45%±8%, respectively). Annexin V was the strongest adhesion blocker at 0.1 and 0.3 Pa (75%±6% and 74%±8%, respectively).

DETAILED DESCRIPTION OF THE INVENTION

The role of RBC adhesion to endothelial cells in the retinal vein occlusion was investigated by the inventors by measuring RBC adhesion to endothelial cells in RVO and exploring the molecular basis of the adhesion process. The inventors assessed RBC adhesion to endothelial cells and adhesion molecule expression among 32 patients with RVO. Patients with disease known to alter RBC adhesion were excluded (n=8), and further investigation was conducted in 20 patients with central retinal vein occlusion (CRVO) and four patients with retinal artery occlusion (RAO), compared with 25 normal subjects. The inventors surprisingly found RBC adhesion to endothelial cells increase in RVO. The inventors also demonstrate that PS RBC and endothelial PS receptor are involved in RBC adhesion to endothelial cells and responsible for CRVO.

Therapeutic Methods and Uses

Accordingly the present invention relates to a method for preventing or treating a retinal vein occlusion in a subject of need thereof comprising the step of administering said subject with an agent that inhibits the binding of phosphatidylserine to phosphatidylserine receptor or an agent that inhibits the phosphatidylserine receptor expression.

As used herein, the term "subject" denotes a mammal. In a preferred embodiment of the invention, a subject according to the invention refers to any subject (preferably human) afflicted with retinal vein occlusion. In a particular embodiment, the subject is afflicted with central retinal vein occlusion. In a particular embodiment, the subject is afflicted with visual loss associated with increased RBC adhesion to endothelial cells.

The method of the invention may be performed for any type of retinal vein occlusion such as revised in the World Health Organisation Classification of retinal vein occlusion and selected from the H34.8 group: "other retinal vascular occlusion"-central retinal vein occlusion, -incipient, -partial, and tributary".

The term "phophatidylserine" has its general meaning in the art and refers to the most abundant negatively charged phospholipid in eukaryotic membranes. Phophatidylserine refers to the anionic phospholipid present exclusively in the inner leaflet of the plasma membrane of a normal cell, phophatidylserine is externalized following cell activation with both physiological and pathologic stimuli such apoptosis.

The term "phophatidylserine receptor" has its general meaning in the art and refers to phophatidylserine receptor such as the phophatidylserine receptor expressed in endothelial cell.

The agent that inhibits the binding of phosphatidylserine to phosphatidylserine receptor may bind to phosphatidylserine or to phosphatidylserine receptor.

The agent that inhibits the binding of phosphatidylserine to phosphatidylserine receptor may be selected form the group consisting of small molecules, antibodies, aptamers, or polypeptides.

The term "small organic molecule" refers to a molecule of a size comparable to those organic molecules generally used in pharmaceuticals. The term excludes biological macromolecules (e. g., proteins, nucleic acids, etc.). Preferred small organic molecules range in size up to about 5000 Da, more preferably up to 2000 Da, and most preferably up to about 1000 Da.

The agent that inhibits the binding of phosphatidylserine to phosphatidylserine receptor may consist in an antibody or antibody fragment directed against phosphatidylserine or phosphatidylserine receptor.

In one embodiment of the antibodies or fragment thereof described herein, the antibody is a monoclonal antibody. In one embodiment of the antibodies or portions thereof described herein, the antibody is a polyclonal antibody. In one embodiment of the antibodies or portions thereof described herein, the antibody is a humanized antibody. In one embodiment of the antibodies or portions thereof described herein, the antibody is a chimeric antibody. In one embodiment of the antibodies or portions thereof described herein, the portion of the antibody comprises a light chain of the antibody. In one embodiment of the antibodies or portions thereof described herein, the portion of the antibody comprises a heavy chain of the antibody. In one embodiment of the antibodies or portions thereof described herein, the portion of the antibody comprises a Fab portion of the antibody. In one embodiment of the antibodies or portions thereof described herein, the portion of the antibody comprises a F(ab')2 portion of the antibody. In one embodiment of the antibodies or portions thereof described herein, the portion of the antibody comprises a Fc portion of the antibody. In one embodiment of the antibodies or portions thereof described herein, the portion of the antibody comprises a Fv portion of the antibody. In one embodiment of the antibodies or portions thereof described herein, the portion of the antibody comprises a variable domain of the antibody. In one embodiment of the antibodies or portions thereof described herein, the portion of the antibody comprises one or more CDR domains of the antibody.

As used herein, "antibody" includes both naturally occurring and non-naturally occurring antibodies. Specifically, "antibody" includes polyclonal and monoclonal antibodies, and monovalent and divalent fragments thereof. Furthermore, "antibody" includes chimeric antibodies, wholly synthetic antibodies, single chain antibodies, and fragments thereof. The antibody may be a human or nonhuman antibody. A nonhuman antibody may be humanized by recombinant methods to reduce its immunogenicity in man.

Antibodies are prepared according to conventional methodology. Monoclonal antibodies may be generated using the method of Kohler and Milstein (1975). To prepare monoclonal antibodies useful in the invention, a mouse or other appropriate host animal is immunized at suitable intervals (e.g., twice-weekly, weekly, twice-monthly or monthly) with antigenic forms of phosphatidylserine or phosphatidylserine receptor. The animal may be administered a final "boost" of antigen within one week of sacrifice. It is often desirable to use an immunologic adjuvant during immunization. Suitable immunologic adjuvants include Freund's complete adjuvant, Freund's incomplete adjuvant, alum, Ribi adjuvant, Hunter's Titermax, saponin adjuvants such as QS21 or Quil A, or CpG-containing immunostimulatory oligonucleotides. Other suitable adjuvants are well-known in the field. The animals may be immunized by subcutaneous, intraperitoneal, intramuscular, intravenous, intranasal or other routes. A given animal may be immunized with multiple forms of the antigen by multiple routes.

Briefly, the antigen may be provided as synthetic peptides corresponding to antigenic regions of interest in phosphatidylserine or phosphatidylserine receptor. Following the immunization regimen, lymphocytes are isolated from the spleen, lymph node or other organ of the animal and fused with a suitable myeloma cell line using an agent such as polyethylene glycol to form a hydridoma. Following fusion, cells are placed in media permissive for growth of hybridomas but not the fusion partners using standard methods, as described (Coding, Monoclonal Antibodies: Principles and Practice: Production and Application of Monoclonal Antibodies in Cell Biology, Biochemistry and Immunology, 3rd edition, Academic Press, New York, 1996). Following culture of the hybridomas, cell supernatants are analyzed for the presence of antibodies of the desired specificity, i.e., that selectively bind the antigen. Suitable analytical techniques include ELISA, flow cytometry, immunoprecipitation, and western blotting. Other screening techniques are well-known in the field. Preferred techniques are those that confirm binding of antibodies to conformationally intact, natively folded antigen, such as non-denaturing ELISA, flow cytometry, and immunoprecipitation.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, L (1991) *Essential Immunology,* 7th Ed., Blackwell Scientific Publications, Oxford). The Fc' and Fc regions, for example, are effectors of the complement cascade but are not involved in antigen binding. An antibody from which the pFc' region has been enzymatically cleaved, or which has been produced without the pFc' region, designated an F(ab')2 fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FRI through FR4) separated respectively by three complementarity determining regions (CDRI through CDRS). The CDRs, and in particular the CDRS regions, and more particularly the heavy chain CDRS, are largely responsible for antibody specificity.

It is now well-established in the art that the non CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody.

This invention provides in certain embodiments compositions and methods that include humanized forms of antibodies. As used herein, "humanized" describes antibodies wherein some, most or all of the amino acids outside the CDR regions are replaced with corresponding amino acids derived from human immunoglobulin molecules. Methods of humanization include, but are not limited to, those described in U.S. Pat. Nos. 4,816,567, 5,225,539, 5,585,089, 5,693,761, 5,693,762 and 5,859,205, which are hereby incorporated by reference. The above U.S. Pat. Nos. 5,585,089 and 5,693,761, and WO 90/07861 also propose four possible criteria which may used in designing the humanized antibodies. The first proposal was that for an acceptor, use a framework from a particular human immunoglobulin that is unusually homologous to the donor immunoglobulin to be humanized, or use a consensus framework from many human antibodies. The second proposal was that if an amino acid in the framework of the human immunoglobulin is unusual and the donor amino acid at that position is typical for human sequences, then the donor amino acid rather than the acceptor may be selected. The third proposal was that in the positions immediately adjacent to the 3 CDRs in the humanized immunoglobulin chain, the donor amino acid rather than the acceptor amino acid may be selected. The fourth proposal was to use the donor amino acid reside at the framework positions at which the amino acid is predicted to have a side chain atom within 3A of the CDRs in a three dimensional model of the antibody and is predicted to be capable of interacting with the CDRs. The above methods are merely illustrative of some of the methods that one skilled in the art could employ to make humanized antibodies. One of ordinary skill in the art will be familiar with other methods for antibody humanization.

In one embodiment of the humanized forms of the antibodies, some, most or all of the amino acids outside the CDR regions have been replaced with amino acids from human immunoglobulin molecules but where some, most or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgG1, IgG2, IgG3, IgG4, IgA and IgM molecules. A "humanized" antibody retains a similar antigenic specificity as the original antibody. However, using certain methods of humanization, the affinity and/or specificity of binding of the antibody may be increased using methods of "directed evolution", as described by Wu et al., (1999), the contents of which are incorporated herein by reference.

Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (KAMA) responses when administered to humans.

In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

Thus, as will be apparent to one of ordinary skill in the art, the present invention also provides for F(ab') 2 Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')2 fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

The various antibody molecules and fragments may derive from any of the commonly known immunoglobulin classes, including but not limited to IgA, secretory IgA, IgE, IgG and IgM. IgG subclasses are also well known to those in the art and include but are not limited to human IgG1, IgG2, IgG3 and IgG4.

In another embodiment, the antibody according to the invention is a single domain antibody. The term "single domain antibody" (sdAb) or "VHH" refers to the single heavy chain variable domain of antibodies of the type that can be found in Camelid mammals which are naturally devoid of light chains. Such VHH are also called "Nanobody®". According to the invention, sdAb can particularly be llama sdAb.

Then after raising antibodies directed against phosphatidylserine or phosphatidylserine receptors as above described, the skilled man in the art can easily select those inhibiting the binding of phosphatidylserine to phosphatidylserine receptor.

In one embodiment, the antibody directed against phosphatidylserine is the antibody 3G4 (bavituximab).

In another embodiment the agent that inhibits the binding of phosphatidylserine to phosphatidylserine receptor is an aptamer. Aptamers are a class of molecule that represents an alternative to antibodies in term of molecular recognition. Aptamers are oligonucleotide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996). Then after raising aptamers directed against phosphatidylserine receptors as above described, the skilled man in the art can easily select those inhibiting the binding of phosphatidylserine to phosphatidylserine receptor.

In another embodiment, agent that inhibits the binding of phosphatidylserine to phosphatidylserine receptor is a polypeptide having the ability to bind PS. In one embodiment of the invention, the agent that inhibits the binding of phosphatidylserine to phosphatidylserine receptor is selected from the group consisting of annexin V (annexin A5, diannexin), annexin peptides, synaptotagmin I, lactadherin, T cell immunoglobulin mucin 1 and 4 (TIM-1, TIM-4), c-carboxyglutamic acid (Gla) containing proteins such as vitamin K-dependent blood coagulation factors.

In another embodiment of the invention, the agent that inhibits the binding of phosphatidylserine to phosphatidylserine receptor is a modified annexin V polypeptide.

In a particular embodiment of the invention, the modified annexin V polypeptide is a polymer of annexin V that has an increased effective size. It is believed that the increase in effective size results in prolonged half-life in the vascular compartment. One such modified annexin V is a dimer of annexin V. In one embodiment, the dimer of annexin V is a homodimer of annexin V. Said homodimer of human annexin V may be prepared using well-established methods of recombinant DNA technology. The annexin V molecules of the homodimer are joined through peptide bonds to a flexible linker. In some embodiments, the flexible linker contains a sequence of amino acids flanked by a glycine and a serine residue at either end to serve as swivels. The linker preferably comprises one or more such "swivels". Preferably, the linker comprises 2 swivels which may be separated by at least 2 amino acids, more particularly by at least 4 amino acids, more particularly by at least 6 amino acids, more particularly by at least 8 amino acids, more particularly by at least 10 amino acids. Preferably, the overall length of the linker is 5-30 amino acids, 5-20 amino acids, 5-10 amino acids, 10-15 amino acids, or 10-20 amino acids. The dimer can fold in such a way that the convex surfaces of the monomer which bind phosphatidylserine, can both gain access to externalized phosphatidylserine. Flexible linkers are well known in the art. Typically a homodimer of annexin V is diannexin as described in Kuypers F A, Larkin S K, Emeis J J, Allison A C. Interaction of an annexin V homodimer (Diannexin) with phosphatidylserine on cell surfaces and consequent antithrombotic activity. Thromb Haemost. 2007 March; 97(3):478-86.

In another embodiment of the invention, modified annexin V polypeptide may consist on a recombinant annexin V expressed with, or chemically coupled to, another protein such as the Fc portion of immunoglobulin. Such expression or coupling increases the effective size of the molecule, preventing the loss of annexin V from the vascular compartment and prolonging the half life of said modified annexin V polypetide.

In one embodiment, agent that inhibits the binding of phosphatidylserine to phosphatidylserine receptor is a functional equivalent of phosphatidylserine receptor or a soluble phosphatidylserine receptor or a soluble truncated phosphatidylserine receptor.

As used herein, a "functional equivalent of phosphatidylserine receptor" is a compound which is capable of binding to phosphatidylserine, thereby preventing its interaction with phosphatidylserine receptor. The term "functional equivalent" includes fragments, mutants, and muteins of phosphatidylserine receptor. The term "functionally equivalent" thus includes any equivalent of phosphatidylserine receptor obtained by altering the amino acid sequence, for example by one or more amino acid deletions, substitutions or additions such that the protein analogue retains the ability to bind to phosphatidylserine. Amino acid substitutions may be made, for example, by point mutation of the DNA encoding the amino acid sequence.

Functional equivalents include molecules that bind phosphatidylserine and comprise all or a portion of the extracellular domains of phosphatidylserine receptor. Typically, said functional equivalents may comprise binding domain of phosphatidylserine receptor or a portion thereof.

The functional equivalents include soluble forms of the phosphatidylserine receptor. A suitable soluble form of these proteins, or functional equivalents thereof, might comprise, for example, a truncated form of the protein from which the transmembrane domain has been removed by chemical, proteolytic or recombinant methods.

Preferably, the functional equivalent is at least 80% homologous to the corresponding protein. In a preferred embodiment, the functional equivalent is at least 90% homologous as assessed by any conventional analysis algorithm such as for example, the Pileup sequence analysis software (Program Manual for the Wisconsin Package, 1996).

The term "a functionally equivalent fragment" as used herein also may mean any fragment or assembly of fragments of phosphatidylserine receptor that binds to phosphatidylserine. Accordingly the present invention provides a polypeptide capable of inhibiting binding of phosphatidylserine receptor to phosphatidylserine, which polypeptide comprises consecutive amino acids having a sequence which corresponds to the sequence of at least a portion of an extracellular domain of phosphatidylserine receptor, which portion binds to phosphatidylserine.

Functionally equivalent fragments may belong to the same protein family as the human phosphatidylserine receptor identified herein. By "protein family" is meant a group of proteins that share a common function and exhibit common sequence homology. Homologous proteins may be derived from non-human species. Preferably, the homology between functionally equivalent protein sequences is at least 25% across the whole of amino acid sequence of the complete protein. More preferably, the homology is at least 50%, even more preferably 75% across the whole of amino acid sequence of the protein or protein fragment. More preferably, homology is greater than 80% across the whole of the sequence. More preferably, homology is greater than 90% across the whole of the sequence. More preferably, homology is greater than 95% across the whole of the sequence.

The polypeptides of the invention may be produced by any suitable means, as will be apparent to those of skill in the art. In order to produce sufficient amounts of polypeptides of the invention, expression may conveniently be achieved by culturing under appropriate conditions recombinant host cells containing the polypeptide of the invention. Preferably, the polypeptide is produced by recombinant means, by expression from an encoding nucleic acid molecule. Systems for cloning and expression of a polypeptide in a variety of different host cells are well known.

When expressed in recombinant form, the polypeptide is preferably generated by expression from an encoding nucleic acid in a host cell. Any host cell may be used, depending upon the individual requirements of a particular system. Suitable host cells include bacteria mammalian cells, plant cells, yeast and baculovirus systems. Mammalian cell lines available in the art for expression of a heterologous polypeptide include Chinese hamster ovary cells, HeLa cells, baby hamster kidney cells and many others. Bacteria are also preferred hosts for the production of recombinant protein, due to the ease with which bacteria may be manipulated and grown. A common, preferred bacterial host is *E coli*.

In specific embodiments, it is contemplated that polypeptides used in the therapeutic methods of the present invention may be modified in order to improve their therapeutic efficacy. Such modification may be used to decrease toxicity, increase circulatory time, or modify biodistribution. For example, the toxicity of potentially important therapeutic compounds can be decreased significantly by combination with a variety of drug carrier vehicles that modify biodistribution.

A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain.

Polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications.

Those of skill in the art are aware of PEGylation techniques for the effective modification of drugs. For example, drug delivery polymers that consist of alternating polymers of PEG and tri-functional monomers such as lysine have been used by VectraMed (Plainsboro, N.J.). The PEG chains (typically 2000 daltons or less) are linked to the a- and e-amino groups of lysine through stable urethane linkages. Such copolymers retain the desirable properties of PEG, while providing reactive pendent groups (the carboxylic acid groups of lysine) at strictly controlled and predetermined intervals along the polymer chain. The reactive pendent groups can be used for derivatization, cross-linking, or conjugation with other molecules. These polymers are useful in producing stable, long-circulating pro-drugs by varying the molecular weight of the polymer, the molecular weight of the PEG segments, and the cleavable linkage between the drug and the polymer. The molecular weight of the PEG segments affects the spacing of the drug/linking group complex and the amount of drug per molecular weight of conjugate (smaller PEG segments provides greater drug loading). In general, increasing the overall molecular weight of the block co-polymer conjugate will increase the circulatory half-life of the conjugate. Nevertheless, the conjugate must either be readily degradable or have a molecular weight below the threshold-limiting glomular filtration (e.g., less than 60 kDa).

In addition, to the polymer backbone being important in maintaining circulatory half-life, and biodistribution, linkers may be used to maintain the therapeutic agent in a pro-drug form until released from the backbone polymer by a specific trigger, typically enzyme activity in the targeted tissue. For example, this type of tissue activated drug delivery is particularly useful where delivery to a specific site of biodistribution is required and the therapeutic agent is released at or near the site of pathology. Linking group libraries for use in activated drug delivery are known to those of skill in the art and may be based on enzyme kinetics, prevalence of active enzyme, and cleavage specificity of the selected disease-specific enzymes. Such linkers may be used in modifying the protein or fragment of the protein described herein for therapeutic delivery.

Another object of the invention relates to a method for treating retinal vein occlusion in a subject of need thereof comprising the step of administering to said subject an agent selected from the group consisting of an inhibitor of phosphatidylserine receptor expression.

The term "expression" when used in the context of expression of a gene or nucleic acid refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include messenger RNAs which are modified, by processes such as capping, polyadenylation, methylation, and editing, and proteins (e.g., phosphatidylserine receptor) modified by, for example, methylation, acetylation, phosphorylation, ubiquitination, SUMOylation, ADP-ribosylation, myristilation, and glycosylation.

An 'inhibitor of expression" refers to a natural or synthetic compound that has a biological effect to inhibit the expression of a gene.

Inhibitors of phosphatidylserine receptor expression for use in the present invention may be based on antisense oligonucleotide constructs. Anti-sense oligonucleotides, including anti-sense RNA molecules and anti-sense DNA molecules, would act to directly block the translation of phosphatidylserine receptor mRNA by binding thereto and thus preventing protein translation or increasing mRNA degradation, thus decreasing the level of phosphatidylserine receptor proteins, and thus activity, in a cell. For example, antisense oligonucleotides of at least about 15 bases and complementary to unique regions of the mRNA transcript sequence encoding phosphatidylserine receptor can be synthesized, e.g., by conventional phosphodiester techniques and administered by e.g., intravenous injection or infusion. Methods for using antisense techniques for specifically alleviating gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as inhibitors of phosphatidylserine receptor expression for use in the present invention. phosphatidylserine receptor gene expression can be reduced by contacting the subject or cell with a small double stranded RNA (dsRNA), or a vector or construct causing the production of a small double stranded RNA, such that phosphatidylserine receptor expression is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes can also function as inhibitors of phosphatidylserine receptor expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of phosphatidylserine receptor mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of phosphatidylserine receptor expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing phosphatidylserine receptor. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in KRIEGLER (A Laboratory Manual," W.H. Freeman C.O., New York, 1990) and in MURRY ("Methods in Molecular Biology," vol. 7, Humana Press, Inc., Cliffton, N. J., 1991).

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g., SAMBROOK et al., "Molecular Cloning: A Laboratory Manual," Second Edition, Cold Spring Harbor Laboratory Press, 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

Pharmaceutical Composition

The agent that inhibits the binding of phosphatidylserine to phosphatidylserine receptor or the agent that inhibits the phosphatidylserine receptor expression of the invention may be used or prepared in a pharmaceutical composition.

In one embodiment, the invention relates to a pharmaceutical composition comprising an agent that inhibits the binding of phosphatidylserine to phosphatidylserine receptor or an inhibitor of phosphatidylserine receptor expression and a pharmaceutical acceptable carrier for use in the prevention or treatment of retinal vein occlusion in a subject of need thereof.

Typically, agent that inhibits the binding of phosphatidylserine to phosphatidylserine receptor or agent that inhibits phosphatidylserine receptor expression may be combined with pharmaceutically acceptable excipients, and optionally sustained-release matrices, such as biodegradable polymers, to form therapeutic compositions.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, intrathecal and intranasal administration forms, local administration in the eyes, and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The agent that inhibits the binding of phosphatidylserine to phosphatidylserine receptor or the agent that inhibits phosphatidylserine receptor expression can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

Pharmaceutical compositions of the invention may include any further agent which is used in the prevention or treatment of retinal vein occlusion. For example, the anti-retinal vein occlusion may include Anticoagulant Agents, Antiaggregating Agents, Fibrinolytic Agents, Thrombolytic Agents, Pentoxyfillin, Troxerutin, Carbonic Anidrase Inhibitors, Steroids, Hemodilution, Protein Kinase C Inhibitors, Hyperbaric Oxygen.

Pharmaceutical compositions of the invention may include any further agent which is used in the prevention or treatment of visual loss associated with increased RBC adhesion to endothelial cells.

In one embodiment, said additional active agents may be contained in the same composition or administered separately.

In another embodiment, the pharmaceutical composition of the invention relates to combined preparation for simultaneous, separate or sequential use in the treatment of retinal vein occlusion.

Pharmaceutical compositions of the inventions may include any other anti-adhesion agents that reduce RBC adhesion to endothelial cells. For example, the anti-adhesion agent may be anti-adhesion molecule antibodies, prostacyclin and/or hydroxycarbamide and combinations thereof. The isolated annexin protein is administered in a range from 0.1 mg/kg to 1.0 mg/kg.

For an adult subject, the modified annexin can be administered in the dosage range of about 1 to about 100 mg.

The annexin dimmer or diannexin is administered in a dose of 10 to 1000 µg/kg.

In other embodiment, the annexin dimmer or diannexin is administered in a dose of 100 to 500 µg/kg.

Prognostics and Diagnostics Methods According to the Invention

A further aspect of the invention relates to a method of identifying a subject having or at risk of having or developing a retinal vein occlusion and/or determining whether the subject will respond to an agent that inhibits the binding of phosphatidylserine to phosphatidylserine receptor or an agent that inhibits phosphatidylserine receptor expression which comprises the step of analyzing a biological sample from said subject for:

(i) determining in a blood sample the level of PS at the surface of RBC (ii) comparing the phophatidylserine level in the blood sample with a control (iii) detecting differential in the phophatidylserine level between the blood sample and the control is indicative of a subject having or at risk of having or developing a retinal vein occlusion.

Analyzing the phophatidylserine level may be assessed by any of a wide variety of well-known methods for measuring phophatidylserine.

In a preferred embodiment, the phophatidylserine level may be measured by fluorescence-activated cell sorting (FACS).

The method of the invention may further comprise a step consisting of comparing the phophatidylserine level in the blood sample with a control, wherein detecting differential in the phophatidylserine level between the blood sample and the control is indicative of a subject having or at risk of having or developing a retinal vein occlusion. The control may consist in blood sample associated with a healthy subject not afflicted with retinal vein occlusion or in a blood sample associated with a subject afflicted with retinal vein occlusion. According to the invention, high phophatidylserine level is indicative of subject having or at risk of having or developing a retinal vein occlusion and low phophatidylserine level is indicative of subject not having or at risk of having or developing a retinal vein occlusion.

Kits

The agent that inhibits the binding of phosphatidylserine to phosphatidylserine receptor or the agent that inhibits the phosphatidylserine receptor expression may be used or prepared in a kit for performing the methods of the invention.

In one embodiment, the invention relates to kits for performing the methods of the invention, wherein said kits comprise an agent selected from the group consisting of agent that inhibits the binding of phosphatidylserine to phosphatidylserine receptor or agent that inhibits phosphatidylserine receptor expression for use in the prevention or treatment of retinal vein occlusion in a subject of need thereof.

A further object of the invention relates to kits comprising a pharmaceutical composition according to the invention and a pharmaceutical acceptable carrier for use in the prevention or treatment of retinal vein occlusion in a subject of need thereof.

The invention will be further illustrated by the figures and the following examples. However, these examples and the figures should not be interpreted in any way as limiting the scope of the present invention.

Example

Material & Methods

Study Population

The study was approved by the Internal Review Boards from participating institutions and signed informed consent was obtained in accordance with the Declaration of Helsinki. Between March 2007 and January 2009, 32 patients with a history of decreased vision due to retinal vascular occlusion were enrolled in the study. The general characteristics and a detailed medical history of the patients were taken at enrollment. Ophthalmological data, including a retinal angiography for each patient, were reviewed by an ophthalmologist. Retinal vein occlusion was diagnosed by the presence of retinal hemorrhages and venous dilation/tortuosity with or without retinal/disc swelling in a defined venous retinal territory: diffuse for CRVO, and located within a hemiretina for hemiretinal vein occlusion (HRVO) or within a retinal quadrant or less for branch retinal vein occlusion (BRVO). Central retinal artery occlusion (CRAO) was diagnosed in patients with a history of sudden vision loss, presence of diffuse retinal pallor with delayed arterial filling during angiography, and a cherry red foveola. We undertook the current blind study to measure RBC adhesion among RVO patients without knowing the ophthalmological diagnosis. We measured RBC adhesion and adhesion molecule expression on RBC. After determining adhesion of RBC and expression of RBC receptor, patient phenotypes were assessed. Two CRVO patients with sickle cell anemia and three with diabetes mellitus, which are known causes of increased RBC adhesion, were excluded. Two patients with BRVO and one with HRVO were also excluded to preserve the homogeneity of the study group. The study group comprised 20 patients with CRVO (Table 1). Their laboratory parameters are presented in Table 2. Four patients with CRAO, three women aged 47, 79 and 84 years and a man aged 95, served as ophthalmological controls. None of the patients had markers of myeloproliferative syndromes. The time between diagnosis and blood sampling varied from 1 month to 3 years. Six patients have been tested at different times after occlusion. No patient was taking an anticoagulant, nine took aspirin and five took troxerutin. The normal healthy controls (n=25) were recruited for a previous study and are members of the medical or laboratory staff of the different institutions (Table 1).

TABLE 1

Clinical characteristics of the study population

| Variable | Patients (n = 20) | Normal subjects (n = 25) |
| --- | --- | --- |
| Men/Women | 10/10 | 14/11 |
| Age at the time of CRVO, median [range], years | 54 [21-75] | 47 [32-63] |
| Body mass index, median [range], kg m$^{-2}$ | 25 [18-29] | 20 [18-24] |
| Arterial hypertension, n (%) | 9 (45) | 0 |
| Dyslipidemia, n (%) | 4 (20) | 0 |
| Diabetes | 0 | 0 |
| Current smokers, n (%) | 2 (10) | 0 |
| Bilateral CRVO, n (%) | 5 (25) | |
| Retinal neovascular complications, n (%) | 5 (25) | |
| Visual acuity* of involved eye, n (%) | | |
| ≤1/10 | 10 (50) | |
| 1/10 to ≤3/10 | 6 (30) | |
| >3/10 | 4 (20) | |
| Chronic open angle glaucoma | 0 | |

*Best corrected visual acuity in case of bilateral CRVO.

TABLE 2

Laboratory parameters of CRVO patients

| | Patients (n = 20) |
| --- | --- |
| Hematocrit, median % [range] | 43.5 [37-50.1] |
| Reticulocytes, median, 10$^3$ mm$^{-3}$ [range] | 71.6 [19.5-105.3] |
| Blood platelet count, median, 10$^3$ mm$^{-3}$ [range] | 260 [184-444] |
| White blood cell count, median, 10$^3$ mm$^{-3}$ [range] | 6.9 [4.6-11.2] |
| Protein C, protein S, or antithrombin deficiency, n (%) | 1 (5) |
| Antiphospholipid antibody*, n (%) | 3 (15) |
| Hyperhomocysteinemia (>15 μmol L$^{-1}$), n (%) | 5 (25) |
| Activated protein C resistance. | 0 |

*Anticardiolipin IgG antibody titer of 12, 19 and 44 UGPL (negative <10, undetermined 10-15 UGPL). None had a positive screening for anti-β2GP1 antibody or lupus anticoagulant.

Erythrocyte Adhesion Measurement

Blood samples were tested after storage at −196° C. as previously described [19]. For the first 10 patients, RBC adhesion (on three occasions, n=30) was measured just after blood sampling and after storage. As the results were similar before and after storage (the interassay coefficient of variation was 13%±2%) all remaining patients were tested after storage.

Static Conditions

RBC adhesion was measured under static conditions using a radiometric technique as previously described [20]. Human microvascular endothelial cells (HMEC-1 Biological Branch Products; CDC, Atlanta, Ga., USA) were cultured in MCDB-131 (Invitrogen, Grand Island, N.Y., USA) supplemented with 15% fetal calf serum (D. Dutscher, Brumath, France), endothelial growth factor (10 ng $mL^{-1}$) and hydrocortisone (1 μg $mL^{-1}$)(Invitrogen). Washed RBCs were resuspended to hematocrit 25% in Hanks Balanced Salt Solution (HBSS) plus 0.5% human serum albumin labeled with $^{51}$chromium, and incubated with HMEC for 30 min at 37° C. Non-adhering RBCs were removed by six successive washes with HBSS and the remaining adherent RBCs were lysed with distilled water. Radioactivity in the lysate was measured in a gamma counter, and adhesion was then calculated as RBCs per square millimeter. In experiments performed to identify the molecular basis of adhesion, a subset of 10 patients, selected as representative of the whole group according to their levels of adhesion, was tested. Inhibition of RBC adhesion was assessed using HMEC preincubated with specific antibodies directed against PS receptor (polyclonal anti-PS receptor antibody, Sigma, St Louis, Mo., USA; polyclonal anti-human stabilin-2 antibody, R&D systems, Minneapolis, Minn., USA) or against human CD36 (monoclonal anti-CD36/SR-B3; R&D systems) or antihuman Brain-specific angiogenesis inhibitor-1 (BAI-1; Santa Cruz Biotechnology, Santa Cruz, Calif., USA). Isotype-matched rabbit IgG, sheep IgG or mouse IgG2b were used as controls as appropriate. In other experiments, a blocking peptide against the PS receptor (PSR (L-20) P; Santa Cruz Biotechnology) was added to HMEC for 1 h at 37° C. and included during the adhesion assay. In some experiments, prior to the adhesion measurement, RBCs were incubated with recombinant, purified annexin V (BD Biosciences, San Jose, Calif., USA).

Flow Conditions

Adhesion of RBCs to HMEC under flow conditions was determined according to a previously published technique [16]. Briefly, HMEC were cultured in gelatin (2%) coated glass capillaries (microslides; Camlab Ltd, Cambridge, UK) for 24 h. Microslides containing confluent HMEC were mounted on the stage of a video-microscope. The RBC suspension (hematocrit 0.5%) was perfused through the microslide at a flow rate equivalent to a wall shear stress of 0.03 Pa for 10 mM, followed by washout of non-adherent cells for 10 min. The wall shear stress was then increased stepwise (from 0.03 to 0.3 Pa) every 5 min. At each step, adherent RBCs were video-recorded in 10 consecutive fields (one field measures 0.1 $mm^2$), then were counted using a computerized image analysis system (Optimas Media Cybernetics, Bethesda, Md., USA; R & D Vision, Paris, France) and expressed as number of RBCs per $mm^2$. Inhibition of RBC adhesion was measured in the presence of the antibodies used in static conditions or after RBC incubation with annexin V.

Measurement of Adhesion Molecules and Phosphatidylserine (PS) on RBCs

The expression of the molecules CD31, CD36, CD47, CD49d, CD71, CD99 (clone TÜ 12) and CD239 was assessed using corresponding specific monoclonal antibodies (Becton Dickinson, San Jose, Calif., USA) and flow cytometry. Acquisition and analysis were performed with the BD FACS Diva software (v6.1.2) on a FACS Canto II flow cytometer (BD Biosciences).

Binding of annexin V-phycoerythrin (PE) (BD Biosciences) to RBC was measured by flow cytometry to determine PS exposure. One million washed RBCs were incubated with annexin V-PE in the presence of either 2.5 mM $CaCL_2$ or 2.5 mM EDTA [21]. The results were expressed as number of positive RBCs and mean fluorescence intensity (MFI). Blood samples (five patients and five controls tested on two occasions, n=10) were tested the day after collection and also after storage. The results of PS-positive cells were similar before and after storage (the interassay coefficient of variation was 0.1%). We decided to test all the patients after storage.

Statistical Analysis

Results are presented either as the mean±standard error of the mean (SEM), or percentiles (10-90%, 25-75%, and external values). Statistical significance was determined using a one-way analysis of variance (ANOVA) followed by the parametric Dunnett's test. Correlation coefficient was calculated using the parametric Pearson's test.

Results

RBC Adhesion to Endothelium

Adhesion of RBC was enhanced in patients with RVO (32 patients, P<0.001).

Patients with CRVO (25 patients) had higher RBC adhesion than patients with RAO (four patients) or BRVO (two patients). One patient with hemiretinal vein occlusion had RBC adhesion similar to patients with CRVO.

Among the 20 CRVO patients selected for further analysis, six have been tested at different time intervals: two patients have been tested 1 and 2 years after the first investigation, one after 2 years and three after 1 or 6 months. There was no significant difference between the samples examined at different times.

Figure 1:
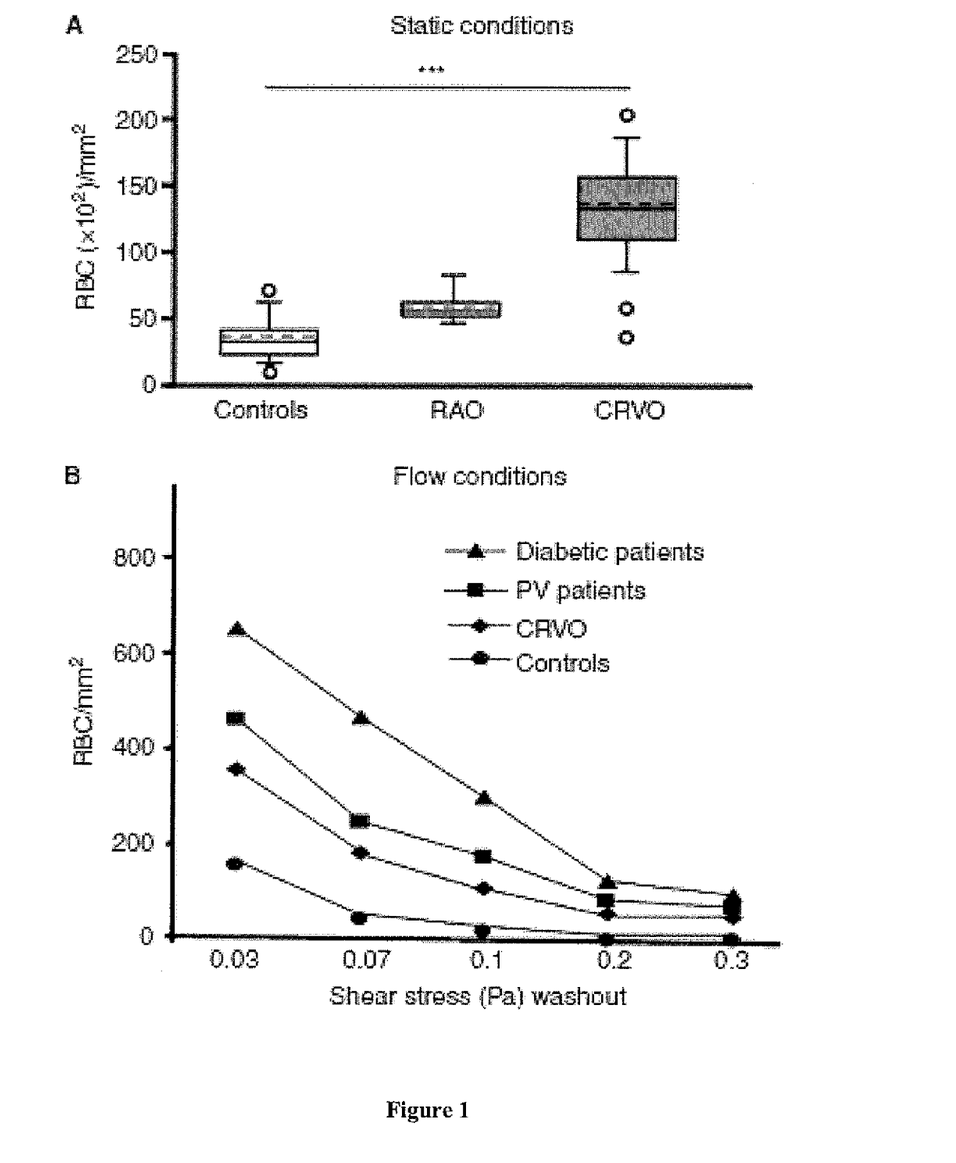

Under static conditions, adhesion of RBCs from patients with CRVO (n=20) to HMEC was significantly increased compared with adhesion of normal RBCs (n=25) and of RBCs from patients with RAO (n=4). The mean number of adhering CRVO RBCs was 135±7·10$^2$ $mm^2$ (mean±SEM) compared with the adhesion of RAO RBCs (63±5·10$^2$ $mm^{-2}$) and normal RBCs (37±3·10$^2$ $mm^2$) (FIG. 1A). A flow-based adhesion assay was used to test the strength of RBC attachment to HMEC by allowing RBCs to adhere at low wall shear stress (0.03 Pa) and then analyzing washout with increasing stress (0.03-0.3 Pa). RBCs from patients with CRVO adhered in greater numbers and were more resistant to washout than control RBCs: at 0.07 Pa, 190±8 and 30±4 $mm^{-2}$ RBCs respectively (P<0.001). The number of RBCs remaining adherent after washout at the highest shear stress (0.3 Pa) was 20±8 $mm^{-2}$ for the patients with CRVO and <1 $mm^{-2}$ for the control group (FIG. 1B). Adhesion of RBCs measured in previous studies [16,22] in Type 2 diabetic patients (n=60) and in patients with polycythemia vera (PV) (n=38) is also presented in FIG. 1(B). The most adherent were RBCs from patients with diabetes. PV RBCs adhere more at low shear stress but similarly at 0.2 and 0.3 Pa compared with CRVO RBCs.

Expression of Adhesion Molecules and Phosphatidylserine (PS) Expression on RBC

The expression of several adhesion molecules was tested by flow cytometry in CRVO, RAO and control RBCs. CD36, CD47, CD49d, CD99 and CD239 were similarly expressed on normal and CRVO or RAO RBCs (no significant difference).

Figure 2:
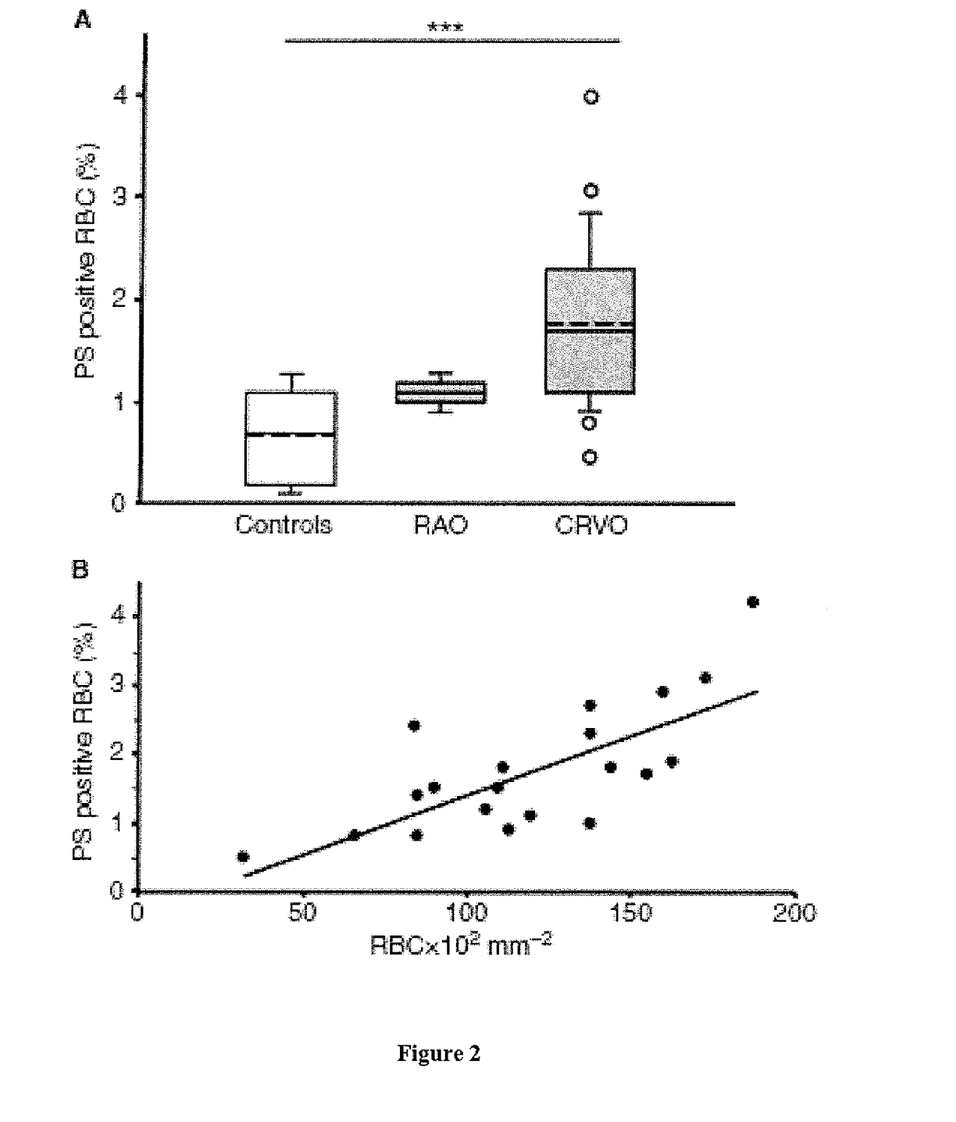
FIG. 2: (A) Detection of phosphatidylserine (PS) exposure on red blood cells (RBCs) by flow cytometry with annexin V-phycoerythrin. PS expression was higher in patients with central retinal vein occlusion (***P<0.001). The percentage of PS-positive RBCs from retinal artery occlusion patients is not statistically different from that of normal subjects. The unbroken line within the box represents the median; the dotted line represents the mean. The vertical lines extending beyond the boxes indicate the 25% and 75% percentiles, while the horizontal bars outside the boxes represent the 10% and 90% percentiles. The open circles indicate the values outside this range. (B) A significant correlation between PS expression and RBC adhesion was observed (Pearson correlation coefficient, r=0.772, P=0.001.).

CRVO patients had a higher number of RBCs expressing membrane phosphatidylserine (1.8%±0.1% positive RBCs) compared with RBCs from normal subjects (0.7%±0.1% positive RBCs, P<0.001) or RAO patients (1.1%±0.1% positive RBCs) (FIG. 2A). The mean fluorescence intensity (MFI) was 3891±208 and 413±21 arbitrary units of fluorescence (AUF) in CRVO patients and normal subjects, respectively. Six patients have been tested on several occasions from 3 months to 2 years after the first investigation. The coefficient of variation was 0.1%±0.03%.

To exclude that microparticles may stick to RBCs and could be responsible for increased PS, we have used a double labelling technique using annexin V (annexin V-PE) and anti-PECAM (CD31, anti-CD31-FITC). None of the RBCs was PECAM positive, excluding that microparticles either from endothelial cells or platelet origin were responsible for PS presence on RBCs. There was no correlation between reticulocyte count and PS expression. Excluding that a high reticulocyte count may be the cause of augmented percentage of PS-positive red blood cells, double labeling with anti-CD71 (anti-CD71-APC-A) and annexin V (annexin V-PE) did not show that CD71-positive RBCs had a higher PS expression.

PS expression and RBC adhesion were measured at the same time in the study group of patients with idiopathic CRVO (n=20). A significant correlation between PS expression and RBC adhesion was observed (Pearson correlation coefficient, r=0.772, P=0.001) and is presented in FIG. 2(B).

Molecular Basis of the Adhesion Process

Figure 3:
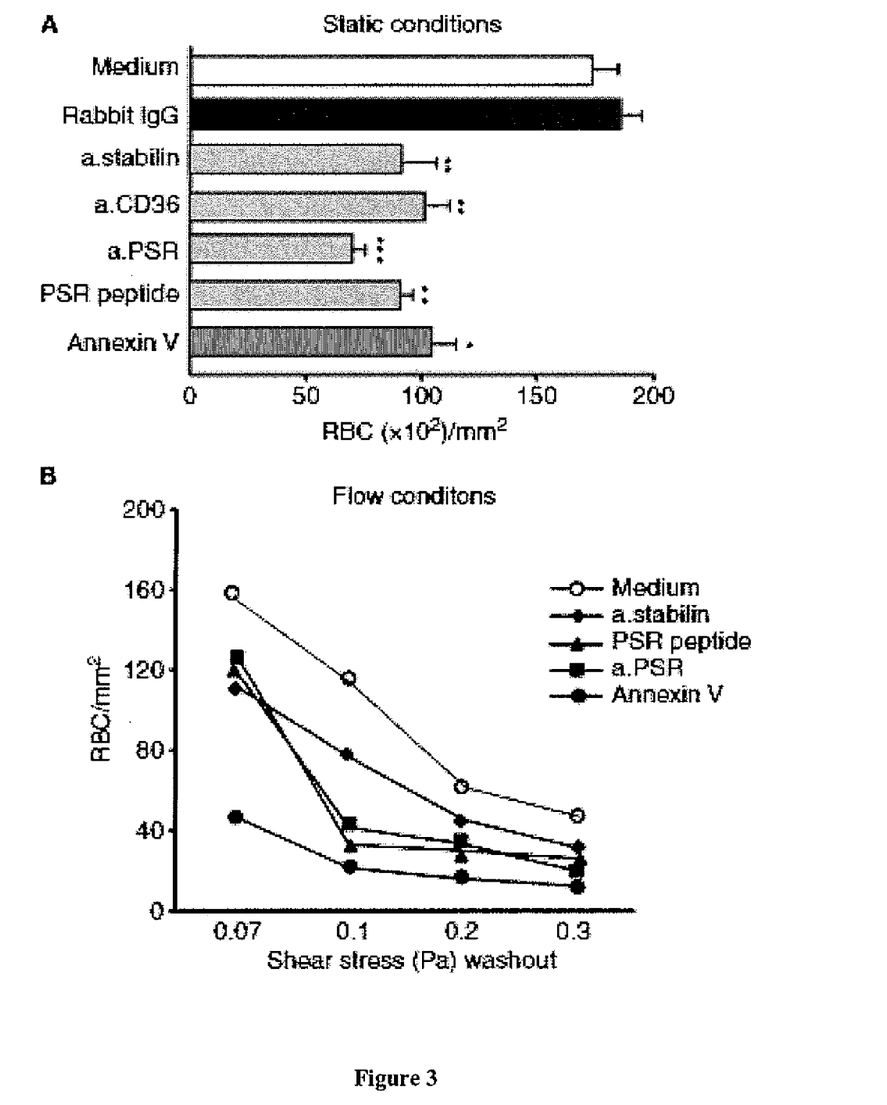

Several molecules have been described as potential receptors or ligands for PS: PS receptor 40 KDa protein, Stabilin-2, BAI-1, and a ubiquitous receptor, CD36 [23]. We tested the effect of antibody in static conditions and flow conditions. Anti-PS receptor, anti-stabilin-2 antibodies or peptide PS receptor inhibited RBC adhesion (FIG. 3A,B). Anti-CD36 was used as a positive control; anti-BAI-1 did not alter the adhesion of CRVO RBCs. Proper isotype control antibodies had no effect. Only rabbit IgG slightly enhanced RBC adhesion (FIG. 3A).

Figure 4:
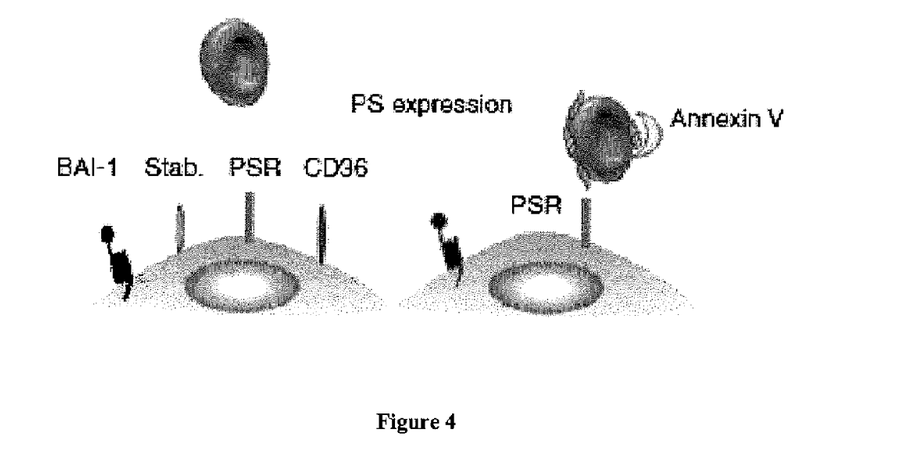
FIG. 4: Schematic representation of adhesion of red blood cells (RBCs) from patients with central retinal vein occlusion (CRVO) to endothelium. Blockade of phosphatidylserine (PS) RBCs and endothelial PS receptor by annexin V or anti-PS receptor indicated that the couple PS-PS receptor is responsible for increased adhesion of RBCs from patients with CRVO.

Except for annexin V, inhibition was similar in static and flow conditions and anti-PSR was the most efficient (in static conditions 55% of inhibition, in flow conditions between 60% and 62% according to the shear stress). PSR peptide inhibited RBC adhesion similarly in flow conditions at 0.1 and 0.2 Pa (70%±2%), and to about the same extent in flow conditions at 0.3 Pa and in static conditions (45% and 41%, respectively). Annexin V is known to bind to PS and when preincubated with RBC from CRVO it reduced the adhesion measured in static conditions (35%, FIG. 3A), while it inhibited RBC adhesion when determined in flow conditions between 60% and 72% according to the shear stress (FIG. 3B). From these results it appears that PS expressed on CRVO RBCs binds to endothelial PS receptors and is responsible for the increased RBC adhesion (FIG. 4).

Discussion

In the present invention, inventors demonstrated that RBC adhesion to endothelial cells was significantly increased in CRVO patients compared with normal subjects. The percentage of PS-positive RBCs was significantly higher in CRVO patients and was correlated with the extent of RBC adhesion. The anti-PS receptor antibodies inhibited 55% of RBC adhesion in static conditions and about 60% in flow conditions. Annexin V, which binds to PS, was the most efficient RBC adhesion blocker in flow conditions (68-74%). These results reinforce the hypothesis that PS exposure on CRVO RBCs is an important parameter for the increased RBC adhesion. No significant difference was observed either in RBC adhesion or PS expression in six patients tested at time of diagnosis and after 3 months to 2 years. These results, concerning only a limited number of patients, do not allow a firm conclusion but suggest that the RBC abnormalities are permanent and not only observed close to the ocular event. In different diseases, RBC adhesion was shown to be a factor responsible for vascular occlusion. Increased exposure of PS was observed in patients with sickle cell disease (SCD) [24] to a similar extent to that found by us in CRVO (2.86% 2% vs. 1.8%+0.1%) and vascular occlusion was only observed in certain circumstances. The percentage of CRVO RBCs that adheres is small and corresponds to 76 000 RBC mm$^{-3}$, which may modify vascular functions. In a rare disease, hereditary hydrocytosis, it was reported that two patients had increased RBC adhesion to endothelial cells as well as membrane phospholipid asymmetry and the authors suggested that the increased adhesion may be related to PS exposure [25]. Phospholipid asymmetry is regulated by an ATP-dependent aminophospholipid translocase (APLT) [26,27]. Asymmetry may be lost by activation of the phospholipid scramblase (PLSCR), which causes nonspecific bidirectional transport of phospholipids across the RBC membrane [28]. It has been postulated that both inhibition of APLT and activation of PLSCR results in PS externalization. Externalization of erythrocyte PS occurs in SCD [29] and may be important in the pathophysiology of vascular dysfunction in SCD and also in CRVO. The observation that RBC PS exposure is increased in patients with CRVO may represent a risk factor that can be easily explored in patients with retinal vascular occlusion. More recently, it was demonstrated that ionophore-treated RBCs or RBCs from patients with SCD bind to endothelium via a specific receptor for PS [30]. As annexin V binds to PS exposed by RBCs, we might expect that PS could also affect annexin V anticoagulant activity.

Increased RBC adhesion to endothelium is also observed in patients with vascular complications in diseases such as SCD, diabetes mellitus and polycythemia vera. Different RBC molecules and different endothelial cell receptors have been identified as being responsible for the abnormal RBC-endothelium interactions. In diabetes mellitus, RBC Band 3 protein is glycated and binds to the receptor for advanced glycation end products (RAGE) [22]. In PV the mutation of the kinase JAK2 results in phosphorylation of LuBCAM (CD239), which is a ligand for the endothelial laminin alpha5 chain [16]. The same RBC molecule, CD239, is implicated in RBC adhesion in SCD [31]. These different examples indicated that RBC adhesion to endothelium may participate in the development of vascular complications in several diseases through different adhesion mechanisms. Our results showed that it may also be a factor that is associated with CRVO.

in SCD and PV a relationship between abnormal erythropoiesis and abnormal RBC behaviour has been proposed [16,31]. Seven patients who participated in a previous study of in vitro bone marrow culture in CRVO patients [15] have been studied for RBC adhesion and PS expression. Five of them showed endogenous erythroid progenitor growth; their results in the present study did not differ from those of the other patients. Further studies are needed to investigate the link between bone marrow progenitor cells and mature red cell abnormalities in CRVO disease.

In SCD, treatment by hydroxyurea reduced RBC adhesion [32]. Hydroxyurea is also the first line treatment of PV patients, reducing the risk of thrombotic events [16]. We can expect that in various diseases with increased RBC adhesion, treatment correcting the RBC abnormalities or modifying adhesion molecule expression may improve the risk of vascular complications.

Modulation of APLT and PLSCR, which regulate phospholipid asymmetry, is a possible candidate for the treatment of patients with CRVO, as is the potential use of annexin V or annexin peptides for masking PS at achievable concentrations.

REFERENCES

Throughout this application, various references describe the state of the art to which this invention pertains. The disclosures of these references are hereby incorporated by reference into the present disclosure.
1. Mitchell P, Smith W, Chang A. Prevalence and associations of retinal vein occlusion in Australia. The Blue Mountains Eye Study. Arch Ophthalmol 1996; 114: 1243-7.
2. Rogers S, McIntosh R L, Cheung N, Lim L, Wang J J, Mitchell P, Kowalski J W, Nguyen H, Wong T Y. The prevalence of retinal vein occlusion: pooled data from population studies from the United States, Europe, Asia, and Australia. Ophthalmology 2010; 117: 313-9.
3. Cahill M T, Fekrat S. Arteriovenous sheathotomy for branch retinal vein occlusion. Ophthalmol Clin North Am 2002; 15: 417-23.
4. Williamson T H. Central retinal vein occlusion: what's the story? Br J Ophthalmol 1997; 81: 698-704.
5. Rehak M, Wiedemann P. Retinal vein thrombosis: pathogenesis and management. J Thromb Haemost 2010; 8: 1886-94.
6. Marcucci R, Bertini L, Giusti B, Brunelli T, Fedi S, Cellai A P, Pali D, Pepe G, Abbate R, Prisco D. Thrombophilic risk factors in patients with central retinal vein occlusion. Thromb Haemost 2001; 86: 772-6.
7. Yasuda M, Kiyohara Y, Arakawa S, Hata Y, Yonemoto K, Doi Y, Iida M, Ishibashi T. Prevalence and systemic risk factors for retinal vein occlusion in a general Japanese population: the Hisayama study. Invest Ophthalmol Vis Sci 2010; 51: 3205-9.
8. Sperduto R D, Hiller R, Chew E, Seigel D, Blair N, Burton T C, Farber M D, Gragoudas E S, Haller J, Seddon J M, Yannuzzi L A. Risk factors for hemiretinal vein occlusion: comparison with risk factors for central and branch retinal vein occlusion: the eye disease case—control study. Ophthalmology 1998; 105: 765-71.
9. Janssen M C, den Heijer M, Cruysberg J R, Wollersheim H, Bredie S J. Retinal vein occlusion: a form of venous thrombosis or a complication of atherosclerosis? A meta-analysis of thrombophilic factors. Thromb Haemost 2005; 93: 1021-6.
10. Chabanel A, Glacet-Bernard A, Lelong F, Taccoen A, Coscas G, Samama M M. Increased red blood cell aggregation in retinal vein occlusion. Br J Haematol 1990; 75: 127 31.
11. Arend O, Remky A, Jung F, Kiesewetter H, Reim M, Wolf S. Role of rheologic factors in patients with acute central retinal vein occlusion. Ophthalmology 1996; 103: 80-6.
12. Williamson T H, Rumley A, Lowe G D. Blood viscosity, coagulation, and activated protein C resistance in central retinal vein occlusion: a population controlled study. Br J Ophthalmol 1996; 80: 203-8.
13. Sofi F, Mannini L, Marcucci R, Bolli P, Sodi A, Giambene B, Menchini U, Gensini G F, Abbate R, Prisco D. Role of haemorheological factors in patients with retinal vein occlusion. Thromb Haemost 2007; 98: 1215-9.
14. Yedgar S, Kaul D K, Barshtein G. RBC adhesion to vascular endothelial cells: more potent than RBC aggregation in inducing circulatory disorders. Microcirculation 2008; 15: 581-3.
15. Heron E, Marzac C, Feldman-Billard S, Girmens J F, Paques M, Delarue R, Piette J C, Casadevall N, Hermine O. Endogenous erythroid colony formation in patients with retinal vein occlusion. Ophthalmology 2007; 114: 2155-61.
16. Wautier M P, El Nemer W, Gane P, Rain J D, Cartron J P, Colin Y, Le Van Kim C, Wautier J L. Increased adhesion to endothelial cells of erythrocytes from patients with polycythemia vera is mediated by laminin alpha5 chain and Lu/BCAM. Blood 2007; 110: 894-901.
17. Wautier M P, Boulanger E, Guillausseau P J, Massin P, Wautier J L. AGEs, macrophage colony stimulating factor and vascular adhesion molecule blood levels are increased in patients with diabetic microangiopathy. Thromb Haemost 2004; 91: 879-85.
18. Hebbel R P, Boogaerts M A, Eaton J W, Steinberg M H. Erythrocyte adherence to endothelium in sickle-cell anemia. A possible determinant of disease severity. N Engl J Med 1980; 302: 992-5.
19. Lelkens C C, Noonnan F, Koning J G, Truijens-de Lange R, Stekkinger P S, Bakker J C, Lagerberg J W, Brand A, Verhoeven A J. Stability after thawing of RBCs frozen with the high- and low-glycerol method. Transfusion 2003; 43: 157-64.
20. Wautier J L, Paton R C, Wautier M P, Pintigny D, Abadie E, Passa P, Caen J P. Increased adhesion of erythrocytes to endothelial cells in diabetes mellitus and its relation to vascular complications. N Engl J Med 1981; 305: 237-42.
21. Kuypers F A, Lewis R A, Hua M, Schott M A, Discher D, Ernst J D, Lubin B H. Detection of altered membrane phospholipid asymmetry in subpopulations of human red blood cells using fluorescently labelled annexin V. Blood 1996; 87: 1179-87.
22. Wautier M P, Khodabandehlou T, Le Devehat C, Wautier J L. Modulation of RAGE expression influences the adhesion of red blood cells from diabetic patients. Clin Hemorheol Microcirc 2006; 35: 379-86.
23. Bratton D L, Henson P M. Apoptotic cell recognition: will the real phosphatidylserine receptor(s) please stand up? Curr Biol 2008; 18: R76-9.
24. Wood B L, Gibson D F, Tait J F. Increased erythrocyte phosphatidylserine exposure in sickle cell disease: flow-cytometric measurement and clinical associations. Blood 1996; 88: 1873-80.
25. Gallagher P G, Chang S H, Rettig M P, Neely J E, Hillery C A, Smith B D, Low P S. Altered erythrocyte endothelial adherence and membrane phospholipid asymmetry in hereditary hydrocytosis. Blood 2003; 101: 4625-7.
26. Barber L A, Palascak M B, Joiner C H, Franco R S. Aminophospholipid translocase and phospholipid scramblase activities in sickle erythrocyte subpopulations. Br J Haematol 2009; 146: 447-55.
27. Soupene E, Kuypers F A. Identification of an erythroid ATP-dependent aminophospholipid transporter. Br J Haematol 2006; 133: 436-8.
28. Wolfs J L, Comfurius P, Rasmussen J T, Keuren J F, Lindhout T, Zwaal R F, Bevers E M. Activated scramblase and inhibited aminophospholipid translocase cause phosphatidylserine exposure in a distinct platelet fraction. Cell Mol Life Sci 2005; 62: 1514-25.
29. Kuypers F A, Yuan J, Lewis R A, Snyder L M, Kiefer C R, Bunyaratvej A, Fucharoen S, Ma L, Styles L, de Jong K, Schrier S L. Membrane phospholipid asymmetry in human thalassemia. Blood 1998; 91: 3044-51.
30. Setty B N, Betal S G. Microvascular endothelial cells express a phosphatidylserine receptor: a functionally active receptor for phosphatidylserine-positive erythrocytes. Blood 2008; 111: 905-14.
31. El Nemer W, Wautier M P, Rahuel C, Gane P, Hermand P, Galacteros F, Wautier J L, Cartron J P, Colin Y, Le Van Kim C. Endothelial Lu/BCAM glycoproteins are novel ligands for red blood cell alpha4beta1 integrin: role in adhesion of sickle red blood cells to endothelial cells. Blood 2007; 109: 3544-51.
32. Bartolucci P, Chaar V, Picot J, Bachir D, Habibi A, Fauroux C, Galacteros F, Colin Y, Le Van Kim C, El Nemer W. Decreased sickle red blood cell adhesion to laminin by hydroxyurea is associated with inhibition of Lu/BCAM protein phosphorylation. Blood 2010; 116: 2152-9.

The invention claimed is:

1. A method for treating a retinal vein occlusion in a subject in need thereof comprising the step of administering to said subject an agent that inhibits binding of phosphatidylserine to phosphatidylserine receptor, wherein said agent consists of annexin V.

2. The method of claim 1, wherein said annexin V is a recombinant or synthetic annexin V peptide or polypeptide.

* * * * *